(12) United States Patent
Hoke et al.

(10) Patent No.: US 10,190,957 B2
(45) Date of Patent: Jan. 29, 2019

(54) CALCULATION-BASED VEHICLE CABIN FILTRATION PERFORMANCE

(71) Applicant: FORD GLOBAL TECHNOLOGIES, LLC, Dearborn, MI (US)

(72) Inventors: Paul Bryan Hoke, Plymouth, MI (US); Lawrence C. Karas, New Boston, MI (US); Manfred Koberstein, Troy, MI (US); Haoliang Michael Sun, Rochester Hills, MI (US)

(73) Assignee: Ford Global Technologies LLC, Dearborn, MI (US)

( * ) Notice: Subject to any disclaimer, the term of this patent is extended or adjusted under 35 U.S.C. 154(b) by 206 days.

(21) Appl. No.: 15/176,413

(22) Filed: Jun. 8, 2016

(65) Prior Publication Data

US 2017/0356835 A1    Dec. 14, 2017

(51) Int. Cl.
| | |
|---|---|
| *G01N 15/08* | (2006.01) |
| *B60H 1/00* | (2006.01) |
| *B60H 3/06* | (2006.01) |
| *G01N 15/06* | (2006.01) |
| *B01D 65/10* | (2006.01) |

(52) U.S. Cl.
CPC ......... *G01N 15/0826* (2013.01); *B60H 1/008* (2013.01); *B60H 1/00735* (2013.01); *B60H 1/00742* (2013.01); *B60H 1/00764* (2013.01); *B60H 1/00985* (2013.01); *B60H 3/06* (2013.01); *G01N 15/06* (2013.01); *B01D 65/10* (2013.01); *B60H 2003/0683* (2013.01); *G01N 2015/0662* (2013.01); *G01N 2015/084* (2013.01)

(58) Field of Classification Search
USPC .......................................................... 702/182
See application file for complete search history.

(56) References Cited

U.S. PATENT DOCUMENTS

| | | | | |
|---|---|---|---|---|
| 5,259,813 A | * | 11/1993 | Abthoff | ................ B60H 3/0085 454/139 |
| 5,564,626 A | * | 10/1996 | Kettler | .................... F24F 3/044 236/49.3 |

(Continued)

FOREIGN PATENT DOCUMENTS

| | | |
|---|---|---|
| CN | 203805673 U | 9/2014 |
| CN | 204084640 U | 1/2015 |

(Continued)

OTHER PUBLICATIONS

English Machine Translation of CN104760490A.

(Continued)

*Primary Examiner* — Paul D Lee
(74) *Attorney, Agent, or Firm* — Vichit Chea; King & Schickli PLLC (57) ABSTRACT

A method for determining a vehicle heating, ventilation, and air conditioning (HVAC) passenger cabin air filter filtration performance includes determining a vehicle-exterior atmospheric particulate contaminant concentration, a passenger cabin air filter efficiency, and an HVAC airflow rate. The passenger cabin particulate contaminant concentration is calculated from the determined atmospheric particulate contaminant concentration, passenger cabin air filter efficiency, and HVAC airflow rate.

19 Claims, 6 Drawing Sheets

(56) References Cited

U.S. PATENT DOCUMENTS

| | | | |
|---|---|---|---|
| 6,758,739 B1* | 7/2004 | Sangwan | B60H 1/008 454/139 |
| 9,764,623 B2* | 9/2017 | Fruehsorger | B60H 3/06 |
| 2004/0031248 A1* | 2/2004 | Lindsay | B01D 46/0023 55/385.3 |
| 2005/0053515 A1* | 3/2005 | Yates | A61L 9/16 422/4 |
| 2006/0154371 A1* | 7/2006 | Organiscak | G01M 3/20 436/3 |
| 2008/0041138 A1* | 2/2008 | Marra | B60H 1/008 73/31.02 |
| 2008/0051021 A1* | 2/2008 | Appelo | G01N 33/0006 454/75 |
| 2009/0309744 A1* | 12/2009 | Fu | G01C 21/3461 340/632 |
| 2011/0015826 A1* | 1/2011 | Ripoll | B60H 1/00735 701/36 |

FOREIGN PATENT DOCUMENTS

| | | |
|---|---|---|
| CN | 204241346 U | 4/2015 |
| CN | 104760490 A | 7/2015 |
| CN | 205019850 U | 2/2016 |
| CN | 205022330 U | 2/2016 |

OTHER PUBLICATIONS

English Machine Translation of CN203805673U.
English Machine Translation of CN204084640U.
English Machine Translation of CN205019850U.
English Machine Translation of CN205022330U.
English Machine Translation of CN204241346U.

* cited by examiner

CALCULATION-BASED VEHICLE CABIN FILTRATION PERFORMANCE

TECHNICAL FIELD

This disclosure relates generally to motor vehicle heating, ventilation, and air-conditioning (HVAC) systems. More particularly, the disclosure relates to methods and systems for determining HVAC system filtration performance and for providing metrics of vehicle passenger cabin air quality.

BACKGROUND

Modern motor vehicle heating, ventilation, and air-conditioning (HVAC) systems are efficient, effective mechanisms for removing vehicle-exterior or ambient air contaminants, conditioning that air as needed, and providing the conditioned air to a motor vehicle passenger cabin. Because vehicle HVAC systems rely solely on ambient air as an air source, they are typically provided with a variety of filters for removing contaminants from ambient air prior to passing the conditioned air to the passenger cabin interior.

Because of global concerns with ambient air quality, particularly in heavily industrialized and populated areas, vehicles may also be provided with sensors for detecting air contaminants. A particular concern in this regard is fine particulate matter (PM) contaminants such as $PM_{2.5}$ particles and $PM_{10}$ particles. However, such sensors are very expensive and disadvantageously only provide highly localized readings, i.e. a measure of air quality only at discrete locations in the passenger cabin rather than a cabin-wide air quality metric. Because of this, in addition to the often prohibitive cost of such sensors, significant engineering challenges are inherent in passenger cabin placement and sampling quality of particulate sensors.

Accordingly, a need is identified in the art for systems and methods for determining passenger cabin air quality. Such methods and systems advantageously should require minimal reliance on expensive particulate sensor technology, and further should allow real-time displays of vehicle interior air quality to vehicle passengers and others.

To solve this and other problems, the present disclosure relates to methods for determining vehicle interior cabin filtration performance and for providing indicators of passenger cabin particulate concentrations, and to systems for implementing the methods. Advantageously, the described systems and methods require minimal sensor technology, and in particular do not rely on expensive automotive grade particulate sensors.

SUMMARY

In accordance with the purposes and benefits described herein, in one aspect a method for determining a vehicle heating, ventilation, and air conditioning (HVAC) passenger cabin air filter filtration performance is described comprising, by at least one vehicle controller comprising a processor, memory, and storage, determining a vehicle-exterior atmospheric particulate contaminant concentration, determining a passenger cabin air filter efficiency, and determining an HVAC airflow rate. These inputs are used to calculate a passenger cabin particulate contaminant concentration. The calculated passenger cabin particulate contaminant concentration may be provided to a user via one or more of an in-vehicle display or a extra-vehicular display. In embodiments, the extra-vehicular display is provided in one or more of a cellular telephone, a smartphone, a mobile computing device, a laptop computing device, and a tablet computing device. The vehicle-exterior atmospheric particulate contaminant concentration in embodiments is retrieved from a remote source or may be directly measured. Contemplated particulate contaminants determined include $PM_{2.5}$ or $PM_{10}$ contaminants.

The step of determining a passenger cabin air filter efficiency may include determining a passenger cabin air filter particulate contaminant load. This may in embodiments include measuring a cabin air filter airflow by an airflow sensor.

In embodiments, the step of determining an HVAC airflow rate comprises one or more of determining an HVAC blower mode, determining an HVAC blower current draw, and detecting an HVAC setting. In embodiments, the HVAC airflow rate may be retrieved from a lookup table comprising a listing of HVAC airflow rates according to one or more of a plurality of HVAC blower modes, a plurality of HVAC blower current draws, and a plurality of HVAC settings, said lookup table being stored in the vehicle controller storage.

In embodiments, inclusion of further inputs is contemplated. This may include determining a passenger cabin interior volume. This may be accomplished by retrieving the passenger cabin interior volume from a lookup table comprising a listing of vehicles and corresponding passenger cabin interior volumes, said lookup table stored in the vehicle controller storage. Another contemplated input is a determined HVAC operation time. Still further, the passenger cabin interior volume could be provided, i.e. hard-coded, as a numerical input in a vehicle control head.

In still other embodiments, the described method includes determining a passenger cabin seal status, which may be provided by one or more sensors associated with one or more of a vehicle passenger cabin window, a vehicle passenger cabin door, a vehicle passenger cabin moonroof, and a vehicle hatch back/lift gate.

In one particular embodiment, the step of calculating an estimated average passenger cabin PM concentration for an HVAC system is performed by the processor according to the general equation: Concentration=Concentration$_{i-1}$*−HVAC outflow+HVAC inflow+Leak effect. For specific HVAC modes, representative algorithms used by the processor are:

Recirculation Mode:

$$C_i = [(C_{i-1}*\text{Vol}) - (H\text{flow}*C_{i-1} - H\text{flow}*C_{i-1}*(1-F\text{eff})) + \text{Leak}*C_{i-1} - \text{Leak}*C_{atmos})*dt]/\text{Vol; and}$$

Fresh Mode:

$$C_i = [(C_{i-1}*\text{Vol}) - (H\text{flow}*C_{i-1} - H\text{flow}*C_{atmos}*(1-F\text{eff})) + \text{Leak}*C_{i-1} - \text{Leak}*C_{atmos})*dt]/\text{Vol}$$

wherein $C_i$=current passenger cabin particulate contaminant concentration; $C_{i-1}$=previous passenger cabin particulate contaminant concentration; Vol =passenger cabin interior volume; Hflow =HVAC airflow rate; Feff =passenger cabin air filter efficiency; Leak =passenger cabin leakage rate; $C_{atmos}$=atmospheric particulate contaminant concentration; dt =time step for the calculation; and tset =time setting for system to initialize or passenger cabin to equilibrate. The skilled artisan will appreciate that if a filtration system time of operation is determined to be less than the time setting required for the system to initialize or the passenger cabin to equilibrate (tset), no reading will be provided (see FIG. 4, ref. num. 414).

In embodiments, still other inputs are contemplated including a determined vehicle rate of travel, a determined number of passenger cabin occupants, and determined vehicle passenger cabin air leakage status. In an embodiment, the vehicle passenger cabin air leakage status is determined by retrieving a leakage value from a lookup table comprising a listing of leakage values according to one or more of a plurality of HVAC settings and a plurality of vehicle speeds, said lookup table being stored in the vehicle controller memory.

In the following description, there are shown and described embodiments of the disclosed systems and methods for determining vehicle interior cabin filtration performance. As it should be realized, the systems and methods are capable of other, different embodiments and its several details are capable of modification in various, obvious aspects all without departing from the devices and methods as set forth and described in the following claims. Accordingly, the drawings and descriptions should be regarded as illustrative in nature and not as restrictive.

BRIEF DESCRIPTION OF THE DRAWINGS

The accompanying drawing figures incorporated herein and forming a part of the specification, illustrate several aspects of the disclosed systems and methods for determining vehicle interior cabin filtration performance, and together with the description serve to explain certain principles thereof. In the drawings.

Reference will now be made in detail to embodiments of the disclosed systems and methods for determining vehicle interior cabin filtration performance, examples of which are illustrated in the accompanying drawing figures.

DETAILED DESCRIPTION

The basic components of a motor vehicle HVAC and air distribution system are well known in the art, and do not require detailed description herein. However, at a high level, with reference to FIG. 1 a motor vehicle HVAC and air distribution system 100 (collectively, HVAC 100) includes at least one ambient air inlet (also referred to as a fresh air inlet) 102 for providing ambient air from an exterior of the vehicle to the vehicle passenger cabin interior. The ambient air inlet 102 typically includes a debris screen 104, and is also typically provided with a cabin air filter 106 for removing smaller particulates from ambient air before dispensing into the passenger cabin.

Figure 1:
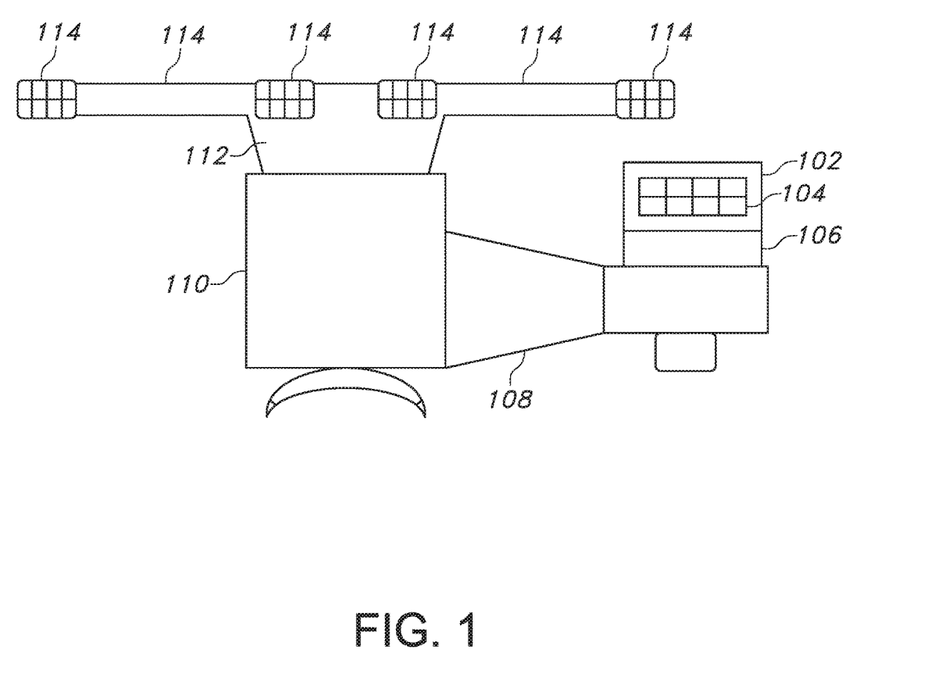
FIG. 1 depicts a representative vehicle HVAC system.

Typically the temperature and volume of air dispensed into the passenger cabin via the HVAC system 100 are controlled. The volume of air is controlled by a blower. The air temperature is controlled by adjusting a ratio of hot air (generated by the HVAC heating elements) and cold air (generated by the HVAC cooling elements) dispensed into the passenger cabin. A portion of these HVAC heating/cooling elements are depicted generally as HVAC evaporator-blower assembly 108. A plenum 110 is provided, which as is known is an air-distribution device for distributing conditioned air to various vehicle dash panel ducts 112. Conditioned air then passes via the panel ducts 112 to one or more register outlets 114, and therefrom into the vehicle passenger cabin.

As is also known, fans (not shown) may be provided to recirculate air from the passenger cabin back through the HVAC components for additional heating or cooling, and then passed back into the passenger cabin. On the other hand, placing the HVAC system 100 in "vent mode" or "fresh mode" allows ambient air to be drawn into the ambient air inlet 102 and passed into the vehicle passenger cabin with or without activating the vehicle HVAC heating and/or cooling elements. In turn, as is also known vehicle HVAC systems can also be set to provide a mixture of ambient air and recirculated air.

Figure 2:
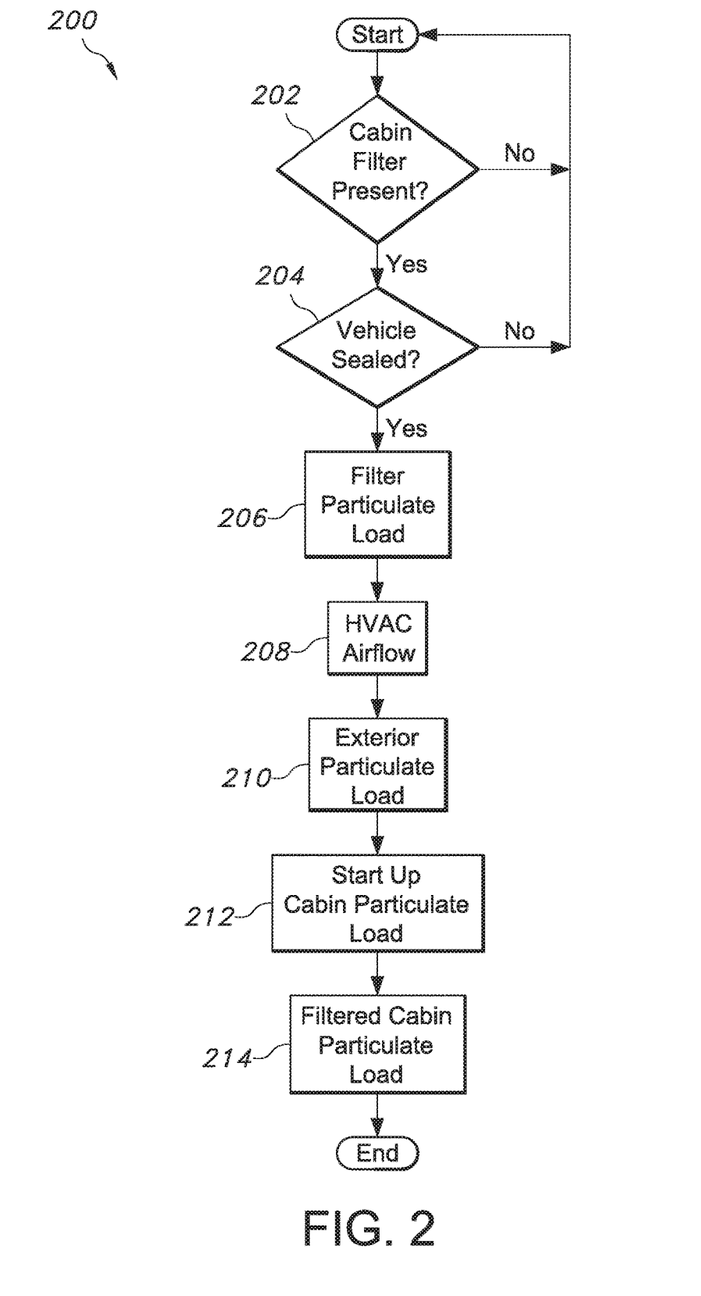
FIG. 2 depicts in flow chart form a method for determining a vehicle interior cabin filtration performance.

At a high level, with reference to FIG. 2 the present disclosure provides a method 200 for determining vehicle interior cabin filtration performance comprising detecting a cabin air filter 106 presence (step 202), determining whether the vehicle is sealed (step 204), determining a cabin air filter 106 contaminant load (step 206), determining an HVAC airflow rate (step 208), and providing externally sourced contaminant date (step 210). As will be appreciated, these steps may be performed sequentially or simultaneously. Finally, these inputs are used to determine a potential vehicle passenger cabin contaminant load at startup (step 212) and also a vehicle passenger cabin contaminant load after cabin filtration (step 214).

Figure 3:
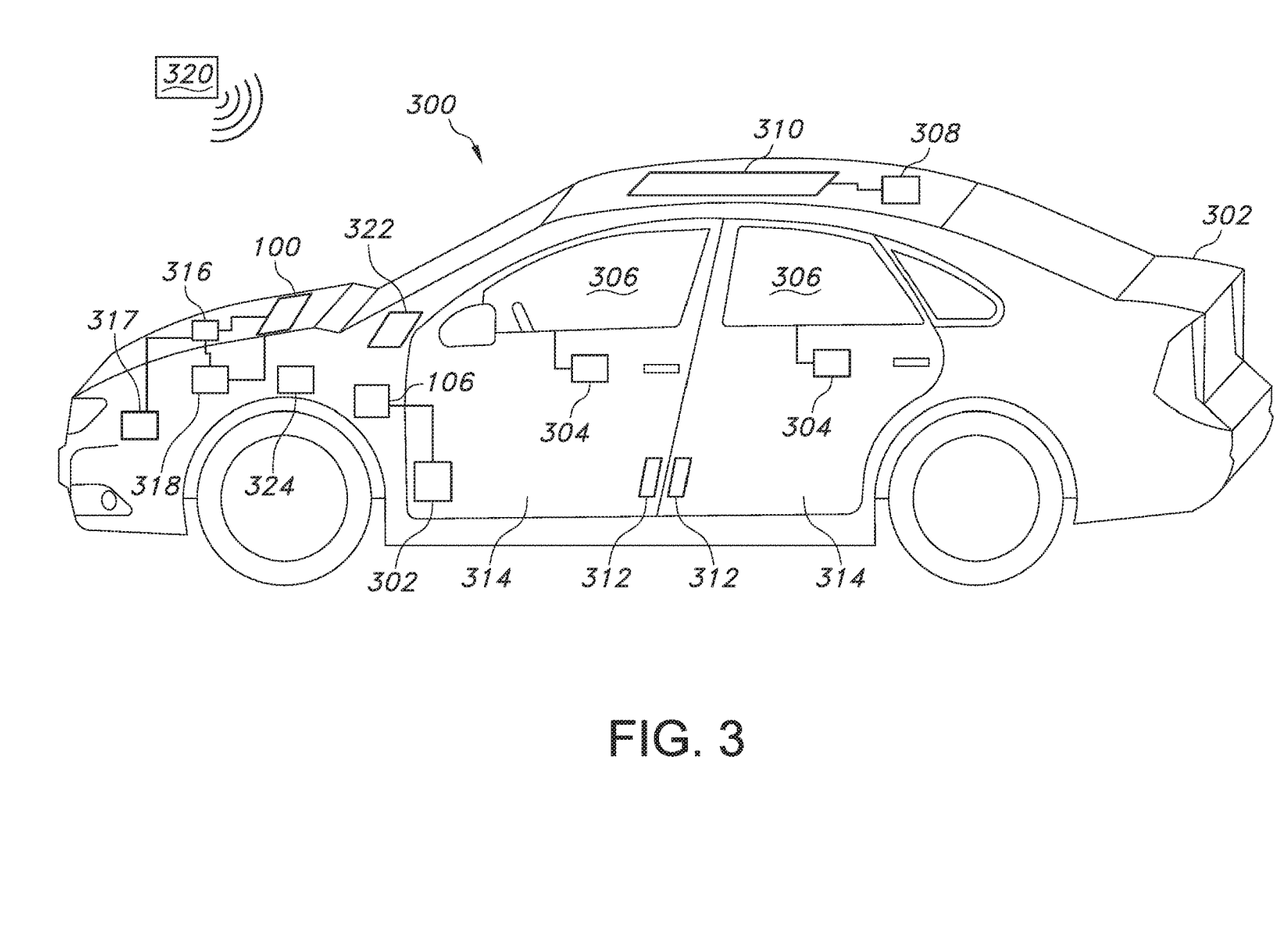
FIG. 3 depicts a representative system for performing the method of FIG. 2.

A representative system 300 for performing the method shown in FIG. 2 is provided in FIG. 3. As shown therein, a vehicle 302 including the system 300 may include one or more cabin air filter life sensors 303 which detect a presence and filter life (contaminant load) of the cabin air filter 106. A non-limiting example of a filter life sensor 303 is an airflow sensor, which extrapolates filter contaminant load and thereby remaining filter life from decreases in airflow through the cabin air filter 106 body. Other sensor-based methods for determining a filter life are known based on estimating filter airflow resistance, including without intending any limitation determining a pressure drop across a filter membrane, determining a current draw of an HVAC blower, and torque sensors for determining an effort of operation of an HVAC blower.

The system also includes one or more cabin sensors for determining a sealed status (or not) of the vehicle. These can include sensors 304 for determining a position (open or closed) of the passenger cabin windows 306, sensors 308 for determining a position of the vehicle moonroof 310, and sensors 312 for determining a position of the vehicle passenger cabin doors 314. The sensors 304, 308, 312 may be simple pressure switches, or may be more elaborate sensor types such as continuity or position sensors.

As noted above, the described method also includes a step 208 of determining an HVAC 100 airflow rate. This may be determined by detecting an HVAC 100 setting, such as by a control module 316, or by detecting a selected HVAC evaporator/blower 108 mode (recirculate, fresh air, etc.) by control module 316. Alternatively or additionally, a sensor 318 may be provided, configured for determining the blower 108 current draw. The control module 316 may be connected to the sensor 318, and may be configured to determine from the sensor-detected current draw a current evaporator/blower 108 mode, such as by accessing a stored lookup table of known HVAC modes vs. evaporator/blower 108 current draws. The control module 316 may be a dedicated controller having a processor, memory, and storage including embedded logic for performing the described calculations. Alternatively or additionally, some or all of the described functions may be provided by higher level vehicle controllers 317, for example an electronic control unit (ECU) control module associated with the vehicle such as the vehicle General Electronic Module (GEM), Body Control Module (BCM), Central Control Module (CCM), or others. In yet another alternative embodiment, the controller 317 may communicate with the control module 316 and/or other elements of the system 300 indirectly via a second or third control module communicating via a vehicle controller area network (CAN), for example, a LIN bus.

As described above, the method also includes a step 210 of determining a vehicle-exterior contaminant load. While this could be determined by dedicated onboard particulate sensors associated with the vehicle, in an embodiment an input of a measure of exterior contaminant load, i.e. ambient pollution or atmospheric particulate contaminant concentration, is provided by an exterior or remote source 320, for example by way of cloud-sourced contaminant data input provided by a commercial source and received by a receiver 322 onboard the vehicle 302, such as a modem or other receiver, including without intending any limitation radio receivers, Bluetooth® receivers, and cellular signal receivers.

Still other inputs and devices for providing such inputs are contemplated. As non-limiting examples, a vehicle speed or rate of travel input may be provided, such as by the vehicle speedometer 324. Vehicle occupancy may be factored in, for example by occupant sensors (not shown) associated with each seat (not shown) of the vehicle. These may be simple pressure switches, or may be more complex sensors. A vehicle air leakage input may be provided to account for the fact that a motor vehicle passenger cabin is rarely a completely sealed environment. This can be directly calculated, or may be determined by way of a lookup table comparing HVAC 100 settings and vehicle speed determined as described above. In addition, a time of operation input is contemplated, for example time of vehicle 302 operation, time of HVAC blower 108 operation, time of vehicle sealing (closing of windows 306, closing of doors 314, closing of moonroof 310, etc.). Cabin volume may be factored in, which would be known from the vehicle 302 specifications and could be provided as part of a lookup table accessible by control module 316 and/or controller 317. Other contemplated inputs include number of vehicle occupants, determined by various means including seat belt monitor switches, on-board cameras (visible or infrared), and others.

Figure 4:
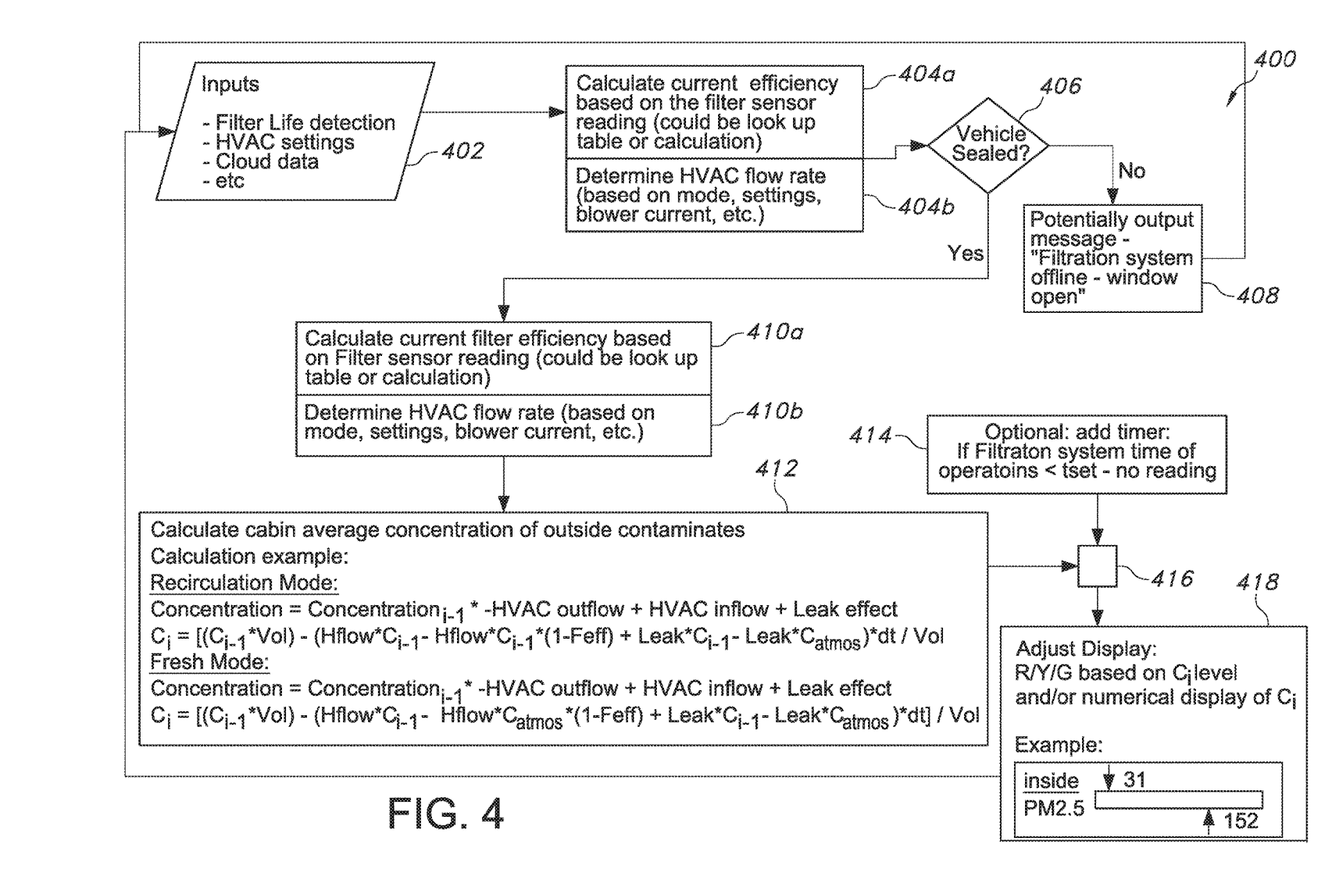
FIG. 4 depicts an alternative embodiment of the method of FIG. 2.

An embodiment of a method 400 for determining vehicle interior cabin filtration performance using the system 300 is shown in FIG. 4. First is a step 402 of gathering various inputs as described above, including at least a determination of cabin air filter 106 life, a determination of HVAC 100 setting, and vehicle-exterior contaminant load. Next, at step 400 pre-vehicle 302 startup determinations are made, to provide a baseline reading of passenger cabin contaminant condition.

At step 404a, a determination is made of cabin air filter 106 efficiency, which may be performed based on a filter sensor 303 reading and calculation based on filter life and the sensor reading, or may simply be determined by stored efficiency vs. filter life vs. contaminant load lookup table. At step 404b, a determination is made of HVAC 100 flow rate, determined as described above by detecting one or more of HVAC mode, setting, blower current draw, and others.

At step 406 a determination is made of whether the vehicle 302 is sealed, such as by determining a position of the vehicle moonroof 310, windows 306, doors 314, etc. by the sensors described above. If the vehicle is determined to be unsealed, the system 300 may output a message indicating that filtration is offline because one of the above elements is in an open configuration (step 408).

If the vehicle 302 is determined to be sealed, at step 410 post-vehicle 302 startup determinations are made. At step 410a, a determination is made of cabin air filter 106 efficiency, which may be performed based on a filter sensor 302 reading and calculation based on filter life and the sensor reading, or may simply be determined by stored efficiency vs. filter life vs. contaminant load lookup table. At step 410b, a determination is made of HVAC 100 flow rate, determined as described above by detecting one or more of HVAC mode, setting, blower current draw, and others. Then, the determinations made at steps 400 and 410 are used to calculate a vehicle 302 passenger cabin average concentration of contaminants at step 412.

The step 412 calculations may be performed for the HVAC blower 108 in recirculation mode and in fresh air mode. The calculation of an estimated average passenger cabin PM concentration for an HVAC system 100 can be summarized as: Concentration=Concentration$_{i-1}$*−HVAC outflow+HVAC inflow+Leak effect. For specific HVAC modes, representative algorithms are:

Recirculation Mode:

$$C_i=[(C_{i-1}*Vol)-(Hflow*C_{i-1}-Hflow*C_{i-1}*(1-Feff)+Leak*C_{i-1}-Leak*C_{atmos})*dt]/Vol; \text{ and}$$

Fresh Mode:

$$C_i=[(C_{i-1}*Vol)-(Hflow*C_{i-1}-Hflow*C_{atmos}*(1-Feff)+Leak*C_{i-1}-Leak*C_{atmos})*dt]/Vol$$

wherein $C_i$=current passenger cabin particulate contaminant concentration; $C_{i-1}$=previous passenger cabin particulate contaminant concentration; Vol=passenger cabin interior volume; Hflow=HVAC airflow rate; Feff=passenger cabin air filter efficiency; Leak=passenger cabin leakage rate; $C_{atmos}$=atmospheric particulate contaminant concentration; dt=time step for the calculation; and tset=time setting for system to initialize or passenger cabin to equilibrate. Each of these calculations may be made by logic programmed into control module 316 and/or controller 317 as described above. The skilled artisan will appreciate that if a filtration system time of operation is determined to be less than the time setting required for the system to initialize or the passenger cabin to equilibrate (tset), no reading will be provided (see FIG. 4, ref. num. 414).

Figure 5A:
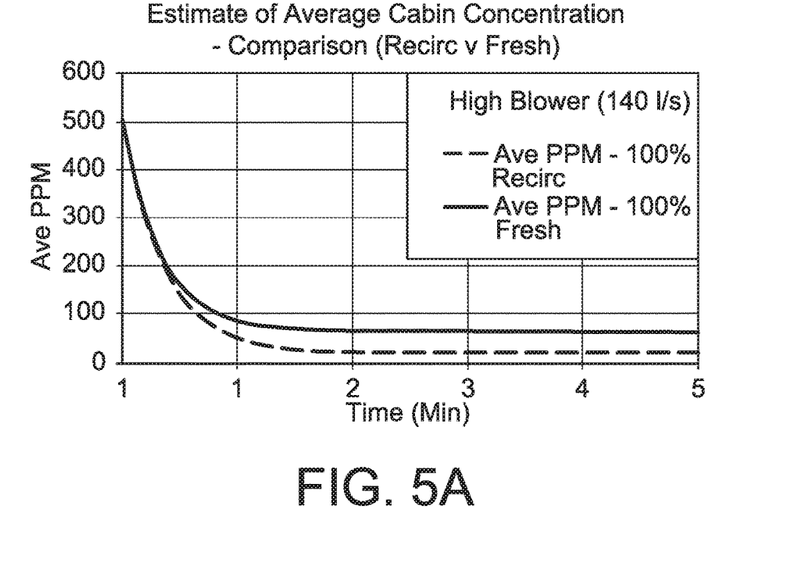
FIG. 5A depicts in graphical form a plot of average passenger cabin particulate concentrations for an HVAC in recirculation mode versus the HVAC in fresh air mode at a high blower setting.
Figure 5B:
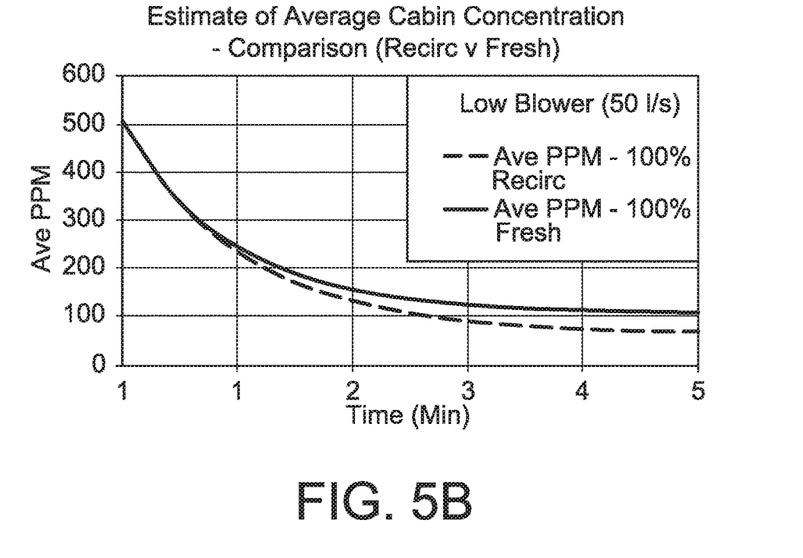
FIG. 5B depicts in graphical form a plot of average passenger cabin particulate concentrations for an HVAC in recirculation mode versus the HVAC in fresh air mode at a low blower setting.

It is contemplated as an optional step (step 414) to provide a timer 416 which issues a signal such as to control module 316 and/or controller 317 to shut the system 400 down if a cabin air filter 106 time of operation is less than a predetermined time for the system 400 to initialize or for the passenger cabin to equilibrate (tset; where tset =time setting for system to initialize or passenger cabin to equilibrate). FIGS. 5A and 5B show plots of representative calculations of estimated average passenger cabin $PM_{2.5}$ concentrations over time of HVAC 100 operation, plotting concentrations for the HVAC in recirculation mode and fresh mode, and comparing HVAC blower 108 high settings (140 1/s, see FIG. 5A) and HVAC blower low settings (50 1/s, see FIG. 5B).

Figure 6:
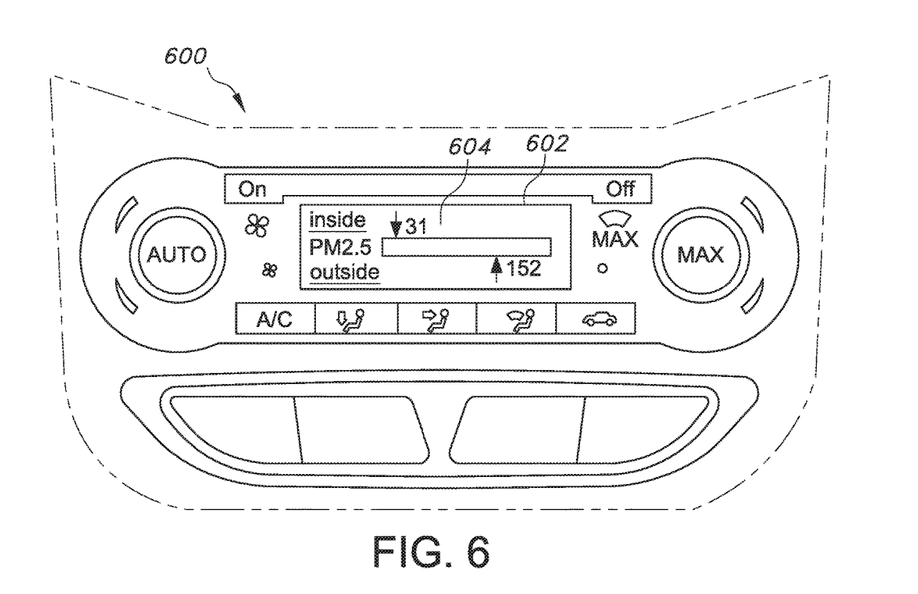
FIG. 6 depicts a representation of vehicle-exterior and calculated vehicle-interior particulate concentrations pushed to a vehicle-associated view screen.
Figure 7:
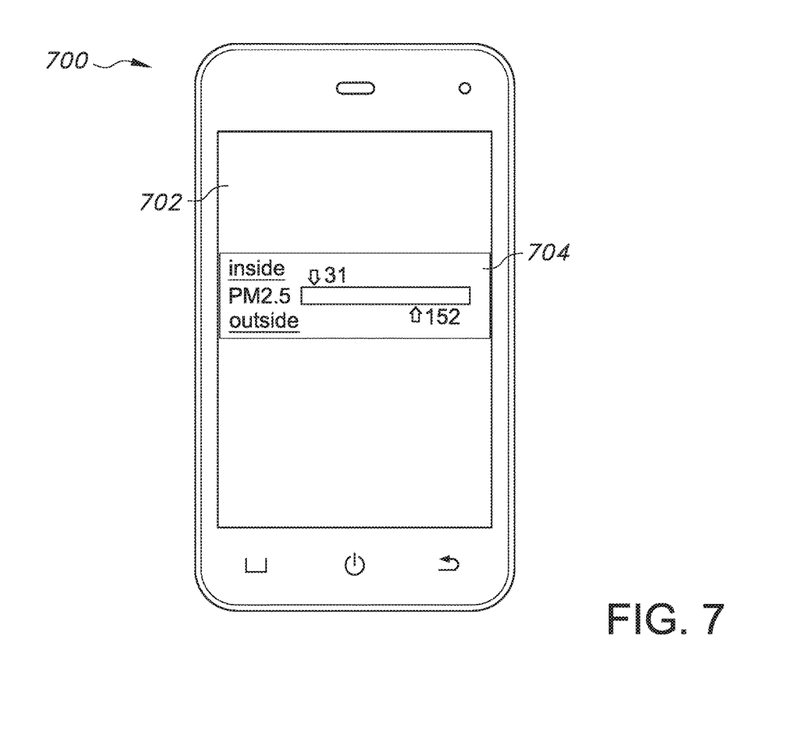
FIG. 7 depicts the representation of vehicle-exterior and calculated vehicle-interior particulate concentrations pushed to a mobile device view screen.

Returning to FIG. 4, as a final step 418 it is contemplated to provide the estimated passenger cabin PM concentrations vs. exterior PM concentrations as a user-viewable display. This can be accomplished by the control module 316 and/or controller 317 pushing the information to a user-viewable screen, for example to a dash panel 600 screen 602 as a graphic 604 (FIG. 6) or to a remotely-located smartphone or other mobile device 700 via an app for display on the screen 702 as a graphic 704.

Obvious modifications and variations are possible in light of the above teachings. All such modifications and variations are within the scope of the appended claims when interpreted in accordance with the breadth to which they are fairly, legally and equitably entitled.

What is claimed:

1. A method for determining a vehicle passenger cabin particulate contaminant concentration value comprising:
    by a vehicle controller including a processor, storage, and memory:
    receiving an input indicative of a vehicle-exterior atmospheric particulate contaminant concentration value from data provided by one or both of a vehicle-mounted particulate sensor or a remotely located particulate sensor;
    receiving an input indicative of a passenger cabin air filter efficiency value from data provided by one or more of a passenger cabin air filter airflow sensor, a heating, air-conditioning, and ventilation (HVAC)-associated torque sensor, an HVAC blower current sensor, and an HVAC mode sensor;
    receiving an input indicative of a vehicle heating, ventilation, and air conditioning (HVAC) airflow rate value from data provided by one or more of an HVAC setting sensor, the HVAC mode sensor, and the HVAC blower current sensor;
    receiving an input indicative of a passenger cabin leakage rate value from data provided by the HVAC setting sensor and a vehicle speed sensor; and
    by the vehicle controller, calculating a passenger cabin particulate contaminant concentration value as a function of the vehicle-exterior atmospheric particulate contaminant concentration value, the passenger cabin air filter efficiency value, the HVAC airflow rate value, and the passenger cabin leakage rate value.

2. The method of claim 1, further including providing the calculated passenger cabin particulate contaminant concentration value to a user via one or more of an in-vehicle display or an extra-vehicular display.

3. The method of claim 1, wherein said vehicle-exterior atmospheric particulate contaminant concentration value is retrieved from the remotely located particulate sensor.

4. The method of claim 3, wherein said vehicle-exterior atmospheric particulate value is determined for one or both of a $PM_{2.5}$ or a $PM_{10}$ contaminant.

5. The method of claim 1, wherein said receiving an input indicative of a passenger cabin air filter efficiency value comprises receiving an input indicative of a passenger cabin air filter particulate contaminant load value from data provided by the passenger cabin air filter airflow sensor.

6. The method of claim 5, including, by the controller, determining said passenger cabin air filter particulate contaminant load for one or both of a $PM_{2.5}$ or a $PM_{10}$ contaminant.

7. The method of claim 5, including providing said input indicative of a passenger cabin air filter contaminant load value by the passenger cabin air filter airflow sensor that determines a cabin air filter airflow rate.

8. The method of claim 5, including providing said input indicative of a passenger cabin air filter contaminant load value by a plurality of passenger cabin air filter airflow sensors that determine a pressure drop across the cabin air filter.

9. The method of claim 1, including, by the controller, retrieving said HVAC airflow rate value from a lookup table comprising a listing of HVAC airflow rates according to one or more of a plurality of HVAC blower modes, a plurality of HVAC blower current draws, and a plurality of HVAC settings, said lookup table being stored in the vehicle controller storage.

10. The method of claim 1, further including, by the controller, determining a passenger cabin interior volume value.

11. The method of claim 10, including, by the controller, retrieving said passenger cabin interior volume value from a lookup table comprising a listing of vehicles and corresponding passenger cabin interior volumes, said lookup table being stored in the vehicle controller storage.

12. The method of claim 1, further including, by the controller, determining an HVAC operation time value.

13. The method of claim 1, further including, by the controller, determining a passenger cabin seal status from data provided by one or more sensors associated with one or more of a vehicle passenger cabin window, a vehicle sun roof/moonroof, and a vehicle passenger cabin door.

14. The method of claim 1, wherein said step of calculating is performed for the HVAC placed in a recirculation mode as:

$$C_i = [(C_{i-1}*\text{Vol}) - (H\text{flow}*C_{i-1} - H\text{flow}*C_{i-1}*(1-F\text{eff}) + \text{Leak}*C_{i-1} - \text{Leak}*C_{atmos})*dt]/\text{Vol}$$

wherein $C_i$=current passenger cabin particulate contaminant concentration; $C_{i-1}$=previous passenger cabin particulate contaminant concentration; Vol=passenger cabin interior volume; Hflow=HVAC airflow rate; Feff=passenger cabin air filter efficiency; Leak=passenger cabin leakage rate; $C_{atmos}$=atmospheric particulate contaminant concentration; dt=time step for the calculation.

15. The method of claim 1, wherein said step of calculating is performed for the HVAC placed in a fresh air mode as:

$$C_i = [(C_{i-1}*\text{Vol}) - (H\text{flow}*C_{i-1} - H\text{flow}*C_{atmos}*(1-F\text{eff}) + \text{Leak}*C_{i-1} - \text{Leak}*C_{atmos})*dt]/\text{Vol}$$

wherein $C_i$=current passenger cabin particulate contaminant concentration; $C_{i-1}$=previous passenger cabin particulate contaminant concentration; Vol=passenger cabin interior volume; Hflow=HVAC airflow rate; Feff=passenger cabin air filter efficiency; Leak=passenger cabin leakage rate; $C_{atmos}$=atmospheric particulate contaminant concentration; dt=time step for the calculation.

16. The method of claim 1, further including, by the controller, determining a number of passenger cabin occupants from inputs provided by one or more occupancy sensors.

17. A method for determining a vehicle passenger cabin particulate contaminant concentration value comprising:
by a vehicle controller including a processor, storage, and memory:
receiving an input indicative of a vehicle-exterior atmospheric particulate contaminant concentration value for one or both of a $PM_{2.5}$ or a $PM_{10}$ contaminant from data provided by a remotely located particulate sensor;
receiving an input indicative of a passenger cabin air filter particular contaminant load for one or both of a $PM_{2.5}$ or a $PM_{10}$ contaminate value from data provided by one or more of a passenger cabin air filter flow sensor, a heating, air-conditioning, and ventilation (HVAC)-associated torque sensor, an HVAC blower current sensor, and an HVAC mode sensor, the input defining a passenger cabin air filter efficiency value;
receiving an input indicative of a vehicle heating, ventilation, and air conditioning (HVAC) airflow rate value from data provided by one or more of an HVAC setting sensor, the HVAC mode sensor, and the HVAC blower current sensor;
receiving an input indicative of a passenger cabin leakage rate value from data provided by the HVAC setting sensor and a vehicle speed sensor; and
by the vehicle controller, calculating a passenger cabin particulate contaminant concentration value as a function of the vehicle-exterior atmospheric particulate contaminant concentration value, the passenger cabin air filter efficiency value, the HVAC airflow rate value, and the passenger cabin leakage rate value.

18. The method of claim 17, wherein said step of calculating is performed for the HVAC placed in a recirculation mode as:

$$C_i = [(C_{i-1}*\text{Vol}) - (H\text{flow}*C_{i-1} - H\text{flow}*C_{i-1}*(1-F\text{eff}) + \text{Leak}*C_{i-1} - \text{Leak}*C_{atmos})*dt]/\text{Vol}$$

wherein $C_i$=current passenger cabin particulate contaminant concentration; $C_{i-1}$=previous passenger cabin particulate contaminant concentration; Vol=passenger cabin interior volume; Hflow=HVAC airflow rate; Feff=passenger cabin air filter efficiency; Leak=passenger cabin leakage rate; $C_{atmos}$=atmospheric particulate contaminant concentration; dt=time step for the calculation.

19. The method of claim 17, wherein said step of calculating is performed for the HVAC placed in a fresh air mode as:

$$C_i = [(C_{i-1}*\text{Vol}) - (H\text{flow}*C_{i-1} - H\text{flow}*C_{atmos}*(1-F\text{eff}) + \text{Leak}*C_{i-1} - \text{Leak}*C_{atmos})*dt]/\text{Vol}$$

wherein $C_i$=current passenger cabin particulate contaminant concentration; $C_{i-1}$=previous passenger cabin particulate contaminant concentration; Vol=passenger cabin interior volume; Hflow=HVAC airflow rate; Feff=passenger cabin air filter efficiency; Leak=passenger cabin leakage rate; $C_{atmos}$=atmospheric particulate contaminant concentration; dt=time step for the calculation.

* * * * *